United States Patent [19]

Yamamoto et al.

[11] Patent Number: 4,745,705
[45] Date of Patent: May 24, 1988

[54] METHOD FOR KILLING INSECTS BY HEATING FUMIGATION

[75] Inventors: Shinobu Yamamoto; Kunihiro Okada; Satoshi Ohi, all of Hiroshima; Shiro Oyama, Urawa; Yasuharu Takei, Hiroshima, all of Japan

[73] Assignee: Sumitomo Chemical Company, Limited, Osaka, Japan

[21] Appl. No.: 73,459

[22] Filed: Jul. 15, 1987

[30] Foreign Application Priority Data

Jul. 18, 1986 [JP] Japan .............................. 61-168120

[51] Int. Cl.$^4$ .......................................... A01M 13/00
[52] U.S. Cl. .................................................. 43/125
[58] Field of Search ................. 43/125, 124, 107, 129

[56] References Cited

U.S. PATENT DOCUMENTS

| | | | |
|---|---|---|---|
| 2,784,466 | 3/1957 | Burns | 43/125 |
| 3,934,023 | 1/1976 | Okuno et al. | 424/274 |
| 4,163,038 | 7/1979 | Nishimura | 43/125 |
| 4,228,124 | 10/1980 | Kashihara | 43/125 |

FOREIGN PATENT DOCUMENTS

| | | |
|---|---|---|
| 36-12459 | 5/1961 | Japan . |
| 43-25081 | 10/1968 | Japan . |
| 43-26274 | 11/1968 | Japan . |
| 44-8361 | 4/1969 | Japan . |
| 45-14913 | 6/1970 | Japan . |
| 45-19801 | 8/1970 | Japan . |
| 45-29244 | 11/1970 | Japan . |
| 46-22585 | 8/1971 | Japan . |
| 52-45768 | 11/1977 | Japan . |
| 55-57502 | 4/1980 | Japan . |
| 59-40409 | 9/1984 | Japan . |
| 60-161902 | 8/1985 | Japan . |
| 60-233001 | 11/1985 | Japan . |
| 61-23163 | 6/1986 | Japan . |

Primary Examiner—Gene P. Crosby
Attorney, Agent, or Firm—Stevens, Davis, Miller & Mosher

[57] ABSTRACT

In a method for knock down of injurious insects or for freeing a particular environment therefrom by heating fumigation comprising dipping a part of a porous absorptive wick in an insecticidal solution to allow it to absorb the solution and indirectly heating said wick around the top to fumigate the absorbed insecticidal solution, a method for knock down of injurious insects or for freeing a particular environment therefrom, which comprises exposing the insects to the vapor, characterized in that a $C_{12}$–$C_{18}$ aliphatic saturated hydrocarbon solution containing as an active ingredient 2-methyl-4-oxo-3-(2-propynyl)cyclopent-2-enyl chrysanthemate is used as said insecticidal solution, a porous absorptive wick prepared by caking a powdery inorganic substance with a binding agent is used as said porous absorptive wick, and besides that said absorptive wick is indirectly heated around the top to a temperature in a range of from 105° to 130° C.

8 Claims, 1 Drawing Sheet

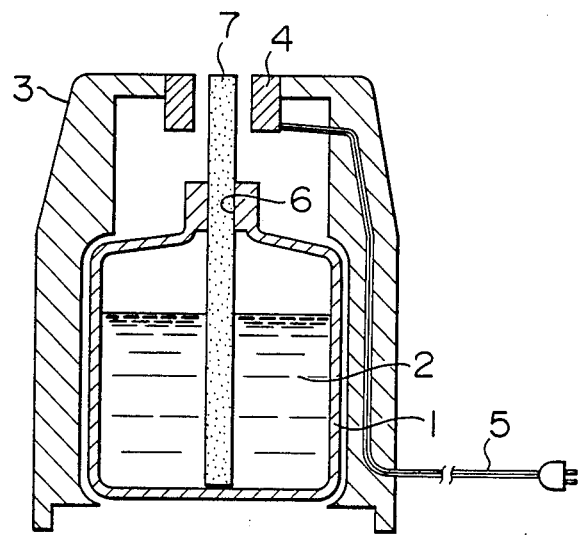

METHOD FOR KILLING INSECTS BY HEATING FUMIGATION

The present invention relates to a method for killing insects by heating fumigation, and more particularly, it relates to a method for killing insects by heating fumigation of such a form that a part of a porous absorptive wick is dipped in an insecticidal solution to allow it to absorb the solution and said wick is indirectly heated at the top to fumigate the absorbed insecticidal solution.

As to a method for killing insects by heating fumigation, an electric fumigator is known as a typical one, but it has defects that the amount of insecticides which can be impregnated into the mat is limited so that exchange of the exhaust mat piece to the new one is essential, the effective percent vaporization of the insecticides impregnated is relatively low, and that it is difficult to maintain a stable insecticidal effect over a long period of time.

For a method of capable overcoming these defects, there is known from of old a method of killing insects by heating fumigation of such a form that a porous absorptive wick is dipped in part in an insecticidal solution to allow it to absorb the solution, and the wick is heated at the top to fumigate the absorbed insecticidal solution. For example, a form of direct heating is disclosed in Japanese Utility Patent Publication No. 25081/1968, but in this form, the decomposition of chemicals is so violent that a form of indirect heating generally tends to be employed. For the form of indirect heating, there are a method of heating with felt, etc. between the absorptive wick and heater (Japanese Utility Patent Publication Nos. 12459/1961 and 22585/1971), and a method of heating with a definite distance between the absorptive wick and heater [Japanese Utility Patent Publication Nos. 26274/1968, 8361/1969, 14913/1970, 19801/1970 and 29244/1970 and Japanese Patent Application Kokai (Laid-open) No. 57502/1980].

In the method of killing insects by heating fumigation which uses the foregoing indirect heating form, the foregoing porous absorptive wick absorbs the insecticidal solution at a relatively high rate because it is generally made of felt, non-woven fabrics, asbestos, etc., so that as the absorptive wick is heated, only the solvent in the insecticidal solution vaporizes and sufficient vaporization of the insecticide becomes difficult. Also, the absorptive wick becomes easy to get blocked because of high-boiling substances formed by the thermal decomposition of the chemicals and ones contained in the solvent, so that it was difficult to maintain a high insecticidal effect over a long period of time.

Further, Japanese Patent Publication No. 23163/1986 proposes a method wherein allethrin or its isomers are used as the insecticide; a solution of the above insecticide in a hydrocarbon solvent having a particular range of boiling point is used as the insecticidal solution, an absorptive wick selected from the group consisting of porous porcelain, those prepared by caking inorganic fibers with gypsum and/or bentonite, said fibers being selected from glass fibers and asbestos, and those prepared by caking powdery inorganic substances with starch, said substances being selected from kaolin, talc, diatomaceous earth, perlite, bentonite, alumina, silica, silica aluminum and titanium, is used as the porous absorptive wick; and the porous absorptive wick is heated at the side of the upper part in a relatively high temperature region of from 130° to 140° C. In the case of heating at such a relatively high temperature, however, there are problems such that the thermal decomposition and polymerization of chemicals becomes violent to lower the percent vaporization of the active ingredient, and also high-boiling substances formed by the thermal decomposition and polymerization accumulate in the absorptive wick to facilitate the blocking of the wick.

Consequently, an object of the present invention is to provide a steady and successive capillary action on the active ingredients through the absorptive wick (a capillary suction method) for killing insects by heating fumigation which can overcome the foregoing problems, does not cause much of blocking of the porous absorptive wick, and yet can effectively fumigate a sufficient amount of insecticide over a long period of time.

The method for killing insects by heating fumigation of the present invention is a method wherein, as described above, a porous absorptive wick is dipped in part in an insecticidal solution to allow it to absorb the solution and it is indirectly heated at the top to fumigate the absorbed insecticidal solution, which method is characterized in that, in order to attain the foregoing object, a $C_{12}$–$C_{18}$ aliphatic saturated hydrocarbon solution containing as an active ingredient 2-methyl-4-oxo-3-(2-propynyl)cyclopent-2-enyl chrysanthemate (hereinafter referred to as active ingredient compound) is used as the insecticidal solution, and that a porous absorptive wick prepared by caking inorganic powders with a binding agent is indirectly heated around the top to a temperature of from 105° to 130° C., preferably 110°–125° C.

The present inventors, in the capillary suction method for killing insects by heating fumigation as described above, found that by using a porous absorptive wick prepared by caking inorganic powders with a binding agent as the porous wick and a $C_{12}$–$C_{18}$ aliphatic saturated hydrocarbon solution containing the foregoing active ingredient compound as the insecticidal solution, the active ingredient compound can be vaporized at a heating temperature of from 105° to 130° C. in a sufficient amount enough to effect an insecticidal activity, and besides that there is little thermal decomposition of the insecticidal component with a high rate of effective evaporation and an effective and stable insecticidal effect can be maintained over a long period of time.

In order to facilite the understanding of the present invention, a drawing of vertical section illustrating one embodiment of apparatus suitable to carry out the method of the present invention will be shown.

In the drawing, 1 is a container containing an insecticidal solution 2 which is attachably and detachably contained and held in a container 3. The container 3 is open at the top, and a circular heater (or a pair of semicircular heaters) 4 is attached to the open part. 5 is a cord connected to the heater 4. The container 1 has an inlet 6 for charging the insecticidal solution, and a porous absorptive wick 7 is held almost air-tightly inside the inlet 6 so that the upper part of the wick 7 is located at the center of the circular heater 4. The drawing given here is one example of apparatus suitable to carry out the method of the present invention, but various forms of apparatus can also be used without being limited to this example.

In the present invention, a $C_{12}$–$C_{18}$ aliphatic saturated hydrocarbon solution containing the foregoing active ingredient compound is used as the insecticidal solution. Said active ingredient compound has geometrical isomers owing to the carboxylic acid moiety and optical isomers owing to the asymmetric carbons of the carboxylic acid and alcohol moieties. In the present invention, these isomers and their mixtures may also be used as an active ingredient. Aliphatic unsaturated hydrocarbons have an offensive odor, so that they are not desirable as a solvent for the insecticidal solution of the present invention, but it doesn't matter if they are contained in the foregoing aliphatic saturated hydrocarbons so long as their amount is of such a degree as not to generate an offensive odor. Among aliphatic saturated hydrocarbons, those having 19 or more carbon atoms have a high viscosity or take a gel form or solidified state, so that smooth absorption of the insecticidal solution by the absorptive wick cannot take place. Consequently, the number of carbon atoms needs to be 18 or less. On the other hand, as is apparent from the examples described later, the total effective percent vaporization of the active ingredient compound tends to lower with a decrease in the number of carbon atoms, so that the number of carbon atoms needs to be 12 or more in order to secure a sufficient percent vaporization. Of course, it doesn't matter if aliphatic hydrocarbons outside the above range are contained so long as their amount is in such a range as not to cause these troubles.

The aliphatic saturated hydrocarbons usable in the present invention include dodecane ($C_{12}$), tridecane ($C_{13}$), tetradecane ($C_{14}$), pentadecane ($C_{15}$), hexadecane ($C_{16}$), heptadecane ($C_{17}$), octadecane ($C_{18}$) and mixture thereof. Commerically available solvents containing these hydrocarbons as a main component may also be used, and they include No. 0 Solvent H (produced by Nippon Oil Co., Ltd.), No. 0 Solvent M (produced by Nippon Oil Co., Ltd.), No. 0 Solvent L (produced by Nippon Oil Co., Ltd.), Normal paraffin (produced by Sanseki, Texaco Chemical Co.), Deotomizole A-1 (produced by Yoshitomi Pharmaceutical Industries, Ltd.), IP Solvent 2028 (produced by Idemitsu Petrochemical Co.), etc.

The concentration of the active ingredient compound in the insecticidal solution, as is apparent from the comparison of percent vaporization described later, is preferably in a range of from 0.5 to 5% by weight, more preferably in a range of from 0.5 to 3% by weight.

In addition to the above active ingredient compound, a stabilizer such as BHT, 2,2'-methylenebis(4-ethyl-6-tert-butylphenol), etc. may be incorporated into the insecticidal solution as need arises. Further, masking agents such as perfumes, etc. may be added.

For the porous absorptive wick, powdery inorganic substances caked with a binding agent and then molded can be used. The powdery inorganic substances include clay, talc, kaolin, diatomaceous earth, gypsum, perlite, bentonite, terra abla, glass fibers, asbestos and their mixtures, etc., and the binding agent includes carboxymethyl cellulose (CMC), starch, gum arabic, gelatin, polyvinyl alcohol (PVA) and their mixtures, etc. Such molded absorptive wicks are finely porous, and the amount of the insecticidal solution absorbed by them is fairly small as compared with absorptive wicks made mainly of fibrous substances, so that they are suitable as an absorptive wick to be used over a long period of time. Among these, gypsum, clay, diatomaceous earth, terra abla and perlite are preferred as the powdery inorganic substance in terms of moldability, etc., and CMC is suitable as the binding agent in terms of insolubility in solvents, moldability, etc. The most preferred absorptive wick is those which are prepared by caking two or more of the above powdery inorganic substances with CMC and molding the resulting cake. In producing such absorptive wicks, the amount of the binding agent used is preferably in a range of from 1 to 10% by weight based on the total weight of the wick.

In the porous absorptive wicks may be incorporated pigments, dyestuffs, antiseptics, etc. as need arises so long as the characteristics of the wicks are not damaged.

As described above, according to the method for killing insects by heating fumigation of the present invention, the above insecticidal compound can be vaporized in an amount enough to display a sufficient insecticidal activity and besides in a high effective percent vaporization at a relatively low heating temperature of from 105° to 130° C., and an effective and stable insecticidal effect can be maintained over a long period of time. Also, according to the method of the present invention, the heating temperature is relatively so low that the method is preferred in terms of safety at the time of use.

REFERENCE EXAMPLE 1

Using an apparatus as shown in the drawing, molded porous absorptive wicks, 7 mm in diameter and 7 cm in length, having compositions shown in Tables 1 and 2 were each dipped in the container containing a liquid $C_{15}$ aliphatic saturated hydrocarbon. The wick was heated around the top to a temperature of 120° C., and the amount of the aliphatic saturated hydrocarbon vaporized (decreased) was measured. The results are shown together in Tables 1 and 2.

TABLE 1

| | Composition | | | | | | |
|---|---|---|---|---|---|---|---|
| | No. 1 | No. 2 | No. 3 | No. 4 | No. 5 | No. 6 | No. 7 |
| Gypsum | 5 | 5 | 5 | 5 | 5 | 5 | 5 |
| Clay | 5 | 5 | 5 | 5 | 5 | 5 | 5 |
| Diatomaceous earth | 3 | 3 | 3 | 3 | 3 | 3 | 3 |
| CMC | 0.1 | 0.3 | 0.5 | 1.0 | 1.5 | 2.0 | 3.0 |
| Amount of solvent vaporized (ml/hr) | 0.22 | 0.18 | 0.16 | 0.11 | 0.08 | 0.03 | 0.01 |

TABLE 2

| | Composition | | | | | | | |
|---|---|---|---|---|---|---|---|---|
| | No. 8 | No. 9 | No. 10 | No. 11 | No. 12 | No. 13 | No. 14 | No. 15 |
| Gypsum | 5 | — | — | 5 | 5 | — | — | 5 |
| Clay | 5 | 5 | 6 | 3 | 5 | 5 | 6 | 3 |
| Terra abla | — | 1 | 1 | — | — | 1 | 1 | — |
| Perlite | — | 5 | 5 | 2 | — | 5 | 5 | 2 |
| Diatomaceous earth | 2 | 1 | — | 2 | 2 | 1 | — | 2 |
| CMC | 0.3 | 0.3 | 0.3 | 0.3 | 0.6 | 0.6 | 0.6 | 0.6 |
| Amount of solvent vaporized (ml/hr) | 0.17 | 0.18 | 0.17 | 0.16 | 0.15 | 0.17 | 0.14 | 0.13 |

As is apparent from the results in Table 1, the amount vaporized and in turn, the amount absorbed tend to decrease with an increase in the amount of CMC incorporated. When the amount of CMC is larger than 1.5 parts by weight (10.3% by weight of the total weight of the wick), the amount of solvent vaporized is markedly small, making it difficult to attain sufficient vaporization. While, in terms of the moldability of the absorptive wick, it is suitable to use CMC in an amount of 1% by weight or more based on the total weight of the wick. Consequently, a suitable amount of said binding agent incorporated is from 1 to 10% by weight based on the total weight of the wick, considering the above absorptivity, moldability, etc.

As is apparent from the results in Table 2, various kinds of powdery inorganic substance can be used and the amount of solvent vaporized is also moderate.

The present invention will be illustrated specifically with reference to the following examples.

EXAMPLE 1

A porous absorptive wick of 7 mm in diameter and 7 cm in length was prepared from a material comprising 5 parts by weight of gypsum, 5 parts by weight of clay, 3 parts by weight of diatomaceous earth and 0.5 part by weight of CMC, and set to the heating fumigator shown in the drawing. In the container was put 10 ml of a $C_{14}$–$C_{17}$ mixed aliphatic saturated hydrocarbon solution [No. 0 Solvent H (as described above] containing 1% by weight of (S)-2-methyl-4-oxo-3-(2-propynyl)cyclopent-2-enyl(1R)-cis, trans-chrysanthemate as an active ingredient compound. Current was passed to the heater to heat the absorptive wick around the top so that the surface of the wick took varying temperatures as shown in Table 3, and the amount vaporized/heating time of the active ingredient compound in the insecticidal solution and the total rate of effective evaporation were measured. Further, a period of time required for the solution to decrease to substantially zero was measured. The results are shown in Table 3. The amount vaporized and total rate of effective evaporation were measured as follows:

Amount vaporized:

Vapor was trapped in succession at regular time intervals by a silica gel-packed column and extracted with chloroform; the chloroform extract was concentrated and quantitatively analyzed by gas chromatography, and the total of the values thus obtained was divided by the total vaporization time.

Total rate of effective evaporation (percent recovery):

The total amount which had been vaporized until the amount vaporized/unit time was substantially zero was obtained by the above test; at the point when the above test was completed, the amount of the active ingredient present in the residual solution in the container (A mg) and that of the active ingredient present in the absorptive wick (B mg = the concentration of the residual solution in the container × increment of the weight of the absorptive wick) were measured; and calculation by the following equation was carried out with the amount of the active ingredient present in the container before heating as C mg:

Total rate of effective evaporation (%) =

$$\frac{\text{Total amount vaporized}}{C - (A + B)} \times 100$$

TABLE 3

| Heating temperature (°C.) | Amount of active ingredient compound vaporized (mg/hr) | Total rate of effective evaporation (%) | Period of time required for the solution to decrease to substantially zero (hr) |
| --- | --- | --- | --- |
| 100 | 0.27 | 73 | 193 |
| 105 | 0.36 | 81 | 162 |
| 110 | 0.41 | 87 | 149 |
| 115 | 0.55 | 84 | 117 |
| 120 | 0.63 | 85 | 95 |
| 125 | 0.72 | 82 | 84 |
| 130 | 0.80 | 80 | 71 |
| 135 | 0.89 | 74 | 58 |
| 140 | 0.95 | 71 | 50 |

As is apparent from the results described above, it was confirmed that the total rate of effective evaporation (percent recovery) is markedly high at a heating temperature of from 105° to 130° C. (both inclusive), the active ingredient compound used being vaporized effectively. At a heating temperature higher than 135° C., the total rate of effective evaporation decreases, that is, resinification by decomposition and polymerization becomes remarkable, and therefore, such temperature proves to be unsuitable. At a temperature lower than 105° C., both the total rate of effective evaporation and the amount of active ingredient compound vaporized/unit time decrease, and therefore, such temperature proves to be unsuitable.

EXAMPLE 2

Procedure was carried out in completely the same manner as in Example 1 except that various aliphatic saturated hydrocarbons different in the number of carbon atoms shown in Table 4 were used, and that the heating temperature was set to 120° C., to measure the amount vaporized and total rate of effective evaporation.

The results are shown in Table 4.

TABLE 4

| Number of carbon atoms of solvent | Amount of active ingredient compound vaporized (mg/hr) | Total rate of effective evaporation (%) |
| --- | --- | --- |
| $C_{11}$ | 0.83 | 72 |
| $C_{12}$ | 0.78 | 80 |
| $C_{14}$ | 0.67 | 83 |
| $C_{16}$ | 0.51 | 83 |
| $C_{18}$ | 0.38 | 81 |

As is apparent from the results in Table 4, the use of $C_{12}$–$C_{18}$ aliphatic saturated hydrocarbons as a solvent was good from the standpoints of the total rate of effective evaporation and the vaporized amount of the active ingredient compound.

EXAMPLE 3

Test was carried out in the same manner as in Example 1 except that the heating temperature was 120° C. and the concentration of the active ingredient compound in the solution was varied as shown in Table 5, to measure the vaporized amount and total rate of effective evaporation of the active ingredient compound. The results are shown in Table 5.

TABLE 5

| Concentration of the active ingredient compound in the solution (wt. %) | Amount of active ingredient compound vaporized (mg/hr) | Total rate of effective evaporation (%) |
| --- | --- | --- |
| 0.5 | 0.58 | 88 |
| 1 | 0.63 | 85 |
| 2 | 0.71 | 83 |
| 3 | 0.79 | 84 |
| 4 | 0.83 | 81 |
| 5 | 0.92 | 80 |
| 10 | 1.07 | 72 |

As is apparent from the results described above, that the concentration of the active ingredient compound-containing solution was in a range of from 0.5 to 5% by weight was good from the standpoints of the total rate of effective evaporation and vaporized amount of the active ingredient compound.

EXAMPLE 4

An absorptive wick (A) of 7 mm in diameter and 7 cm in length was prepared by caking 7 parts by weight of gypsum, 5 parts by weight of clay and 1 part by weight of powdery glass fiber (100 mesh through) with 0.3 part of CMC. Similarly, an absorptive wick (B) of the same size was prepared by caking 2 parts by weight of glass fiber with 10 parts by weight of gypsum. Each absorptive wick was set to the heating fumigator shown in the drawing wherein the wick was to be heated to 110° C. In the container was put 10 ml of a $C_{14}$–$C_{17}$ mixed aliphatic hydrocarbon solution [No. 0 Solvent H (as described above)] containing 1% by weight of (S)-2-methyl-4-oxo-3-(2-propynyl)cyclopent-2-enyl(1R)-cis,trans-chrysanthemate (prallethrin). Using the preparation obtained, the amount of prallethrin vaporized was measured every time 20, 40, 60, 80 and 100 hours elapsed after supplying electric current to the heating fumigator.

TABLE 6

| Time elapsed after supplying electric current (hour) | Amount of prallethrin vaporized (mg/hr) | |
| --- | --- | --- |
| | Absorptive wick (A) | Absorptive wick (B) |
| 20 | 0.47 | 0.84 |
| 40 | 0.51 | 0.63 |
| 60 | 0.43 | 0.50 |
| 80 | 0.46 | 0.42 |
| 100 | 0.42 | No remaining insecticidal solution |

This result shows that the absorptive wick (A) is suitable for the present preparation with prallethrin as an active ingredient, and that the absorptive wick (B) is not suitable therefor.

EXAMPLE 5

A porous absorptive wick of 7 mm in diameter and 7 cm in length was prepared from a material comprising 7 parts by weight of gypsum, 4 parts by weight of clay, 2 parts by weight of diatomaceous earth and 0.4 part by weight of CMC, and set to the heating fumigator shown in the drawing wherein the wick was to be heated to 115° C. In the container was put 15 ml each of $C_{14}$–$C_{17}$ mixed aliphatic hydrocarbon solutions [No. 0 Solvent H (as described above)] containing 200 mg of (S)-2-methyl-4-oxo-3-(2-propynyl)cyclopent-2-enyl(1R)-cis,trans-chrysanthemate (prallethrin) and 200 mg of dl-3-allyl-2-methylcyclopent-2-ene-4-one-1-yl d-cis/trans-chrysanthemate (d-allethrin), respectively. Using every preparation, the knock-down time of mosquito female adults (*Culex pipiens pallens*) was measured as follows according to the room test: Every time 0, 1, 3, 6 and 12 hours elapsed after supplying electric current to a heating fumigator placed in a 8-tatami room (30 m³), 50 female adults of mosquito were released in the room to examine the 50% knock-down time. This test was repeated five times, and the result was expressed by the mean value.

TABLE 7

| Time elapsed after supplying electric current (hour) | Knock-down time (KT50) | |
| --- | --- | --- |
| | Prallethrin | d-Allethrin |
| 0 | 15' 24" | 51' 43" |
| 1 | 1' 54" | 4' 11" |
| 3 | 1' 47" | 4' 22" |
| 6 | 1' 45" | 3' 49" |
| 12 | 1' 55" | 4' 16" |

This result shows that prallethrin is suitable for an active ingredient of the present preparation, and the d-allethrin is not suitable therefor.

What is claimed is:

1. In a method for knock down of injurious insects or for freeing a particular environment therefrom by heating fumigation comprising dipping a part of a porous absorptive wick in an insecticidal solution to allow it to absorb the solution and indirectly heating said wick around the top to fumigate the absorbed insecticidal solution, a method for knock down of injurious insects or for freeing a particular environment therefrom, which comprises exposing the insects to the vapor, characterized in that a $C_{12}$–$C_{18}$ aliphatic saturated hydrocarbon solution containing as an active ingredient 2-methyl-4-oxo-3-(2-propynyl)cyclopent-2-enyl chrysanthemate is used as said insecticidal solution, a porous absorptive wick prepared by caking a powdery inorganic substance with a binding agent is used as said porous absorptive wick, and besides that said absorptive wick is indirectly heated around the top to a temperature in a range of from 105° to 130° C.

2. The method according to claim 1, wherein the insecticidal solution containing from 0.5 to 5% by weight of 2-methyl-4-oxo-3-(2-propynyl)cyclopent-2 enyl chrysanthemate.

3. The method according to claim 1, wherein (S)-2-methyl-4-oxo-3-(2-propynyl)cyclopent-2-yl chrysanthemate is contained as an active ingredient.

4. The method according to claim 1, wherein the powdery inorganic substance is clay, talc, kaolin, diatomaceous earth, gypsum, perlite, bentonite, terra abla, glass fibers, asbestos or their mixtures.

5. The method according to claim 1, wherein the binding agent is carboxymethyl cellulose, starch, gum arabic, gelatin, polyvinyl alcohol or their mixtures.

6. The method according to claim 4, wherein the porous absorptive wick is prepared by caking two or more powdery inorganic substances selected from the group consisting of gypsum, clay, terra abla, perlite and diatomaceous earth with carboxymethyl cellulose.

7. The method according to claim 1, wherein the porous absorptive wick is prepared by caking a powdery inorganic substance with carboxymethyl cellulose of from 1 to 10% by weight based on the total weight of the wick.

8. The method according to claim 5, wherein the porous absorptive wick is prepared by caking two or more powdery inorganic substances selected from the group consisting of gypsum, clay, terra abla, perlite and diatomaceous earth with carboxymethyl cellulose.

* * * * *